United States Patent
Pagoulatos et al.

(10) Patent No.: US 11,647,992 B2
(45) Date of Patent: May 16, 2023

(54) SYSTEM AND METHOD FOR FUSING ULTRASOUND WITH ADDITIONAL SIGNALS

(71) Applicant: EchoNous, Inc., Redmond, WA (US)

(72) Inventors: Nikolaos Pagoulatos, Kirkland, WA (US); Ramachandra Pailoor, Woodinville, WA (US); Greg Nieminen, Bothell, WA (US); Terry Doherty, Snohomish, WA (US); Ron Broad, Arlington, WA (US); Shelby Brunke, Sammamish, WA (US)

(73) Assignee: EchoNous, Inc., Redmond, WA (US)

( * ) Notice: Subject to any disclaimer, the term of this patent is extended or adjusted under 35 U.S.C. 154(b) by 247 days.

(21) Appl. No.: 17/135,760

(22) Filed: Dec. 28, 2020

(65) Prior Publication Data

US 2021/0186466 A1 Jun. 24, 2021

Related U.S. Application Data

(63) Continuation of application No. 16/715,956, filed on Dec. 16, 2019, now Pat. No. 10,874,377, which is a
(Continued)

(51) Int. Cl.
*A61B 7/04* (2006.01)
*A61B 5/00* (2006.01)
(Continued)

(52) U.S. Cl.
CPC .......... *A61B 8/5284* (2013.01); *A61B 5/0006* (2013.01); *A61B 5/0205* (2013.01);
(Continued)

(58) Field of Classification Search
CPC ............ A61B 5/04012; A61B 5/04085; A61B 5/14551; A61B 5/0404; A61B 5/0205;
(Continued)

(56) References Cited

U.S. PATENT DOCUMENTS

| 3,954,098 A | 5/1976 | Dick et al. |
| 4,100,916 A | 7/1978 | King |

(Continued)

FOREIGN PATENT DOCUMENTS

| EP | 3 191 062 B1 | 3/2021 |
| JP | 10-127626 A | 5/1998 |

(Continued)

OTHER PUBLICATIONS

Chinese Search Report for CN Application No. 2018800649579, dated May 10, 2022, 2 pages.
(Continued)

*Primary Examiner* — Boniface Ngathi N
(74) *Attorney, Agent, or Firm* — Seed Intellectual Property Law Group LLP

(57) ABSTRACT

Systems, methods and devices for providing combined ultrasound, electrocardiography, and auscultation data are provided. One such system includes an ultrasound sensor, an electrocardiogram (EKG) sensor, an auscultation sensor, and a computing device. The computing device includes memory and a processor, and the processor receives signals from the ultrasound sensor, the EKG sensor, and the auscultation sensor. Artificial intelligence techniques may be employed for automatically analyzing the data obtained from the ultrasound sensor, the EKG sensor, and the auscultation sensor and producing a clinically-relevant determination based on a combined analysis of the data.

19 Claims, 5 Drawing Sheets

Related U.S. Application Data continuation of application No. 15/969,632, filed on May 2, 2018, now Pat. No. 10,507,009.

(60) Provisional application No. 62/568,709, filed on Oct. 5, 2017.

(51) Int. Cl.

| | | |
|---|---|---|
| A61B 8/00 | (2006.01) | |
| A61B 5/316 | (2021.01) | |
| A61B 5/332 | (2021.01) | |
| A61B 5/282 | (2021.01) | |
| A61B 5/333 | (2021.01) | |
| A61B 5/339 | (2021.01) | |
| A61B 8/08 | (2006.01) | |
| A61B 5/1455 | (2006.01) | |
| A61B 5/0205 | (2006.01) | |

(52) U.S. Cl.
CPC .......... *A61B 5/14551* (2013.01); *A61B 5/282* (2021.01); *A61B 5/316* (2021.01); *A61B 5/332* (2021.01); *A61B 5/333* (2021.01); *A61B 5/339* (2021.01); *A61B 5/7264* (2013.01); *A61B 7/04* (2013.01); *A61B 8/4416* (2013.01); *A61B 8/4427* (2013.01); *A61B 8/4472* (2013.01); *A61B 8/463* (2013.01); *A61B 2562/0219* (2013.01); *A61B 2562/0247* (2013.01)

(58) Field of Classification Search
CPC ..... A61B 5/7264; A61B 5/0006; A61B 5/044; A61B 5/0432; A61B 8/5284; A61B 8/4427; A61B 8/463; A61B 8/4472; A61B 8/4416; A61B 7/04; A61B 2562/0247; A61B 2562/0219

See application file for complete search history.

(56) References Cited

U.S. PATENT DOCUMENTS

| | | |
|---|---|---|
| 4,154,230 A | 5/1979 | Lee |
| 4,304,240 A | 12/1981 | Perlin |
| 4,515,164 A | 5/1985 | Slavin |
| 4,572,202 A | 2/1986 | Thomenius |
| 4,592,236 A | 6/1986 | Battagin et al. |
| 4,651,716 A | 3/1987 | Forester et al. |
| 5,159,931 A | 11/1992 | Pini |
| 5,178,149 A | 1/1993 | Imburgia et al. |
| 5,295,486 A | 3/1994 | Wollschläger et al. |
| 5,360,005 A | 11/1994 | Wilk |
| 5,398,691 A | 3/1995 | Martin et al. |
| 5,539,831 A | 7/1996 | Harley |
| 5,690,111 A | 11/1997 | Tsujino |
| 5,749,833 A | 5/1998 | Hakki et al. |
| 5,812,678 A | 9/1998 | Scalise et al. |
| 5,960,089 A | 9/1999 | Bouricius et al. |
| 6,139,500 A | 10/2000 | Clark |
| 6,152,884 A | 11/2000 | Bjørgaas |
| 6,213,944 B1 | 4/2001 | Miller et al. |
| 6,454,716 B1 | 9/2002 | Zumeris |
| 6,514,201 B1 | 2/2003 | Greenberg |
| 6,547,730 B1 | 4/2003 | Lin et al. |
| 6,624,551 B2 | 9/2003 | Orten |
| 6,626,831 B2 | 9/2003 | Holley et al. |
| 6,673,017 B1 | 1/2004 | Jackson |
| 6,773,398 B2 | 8/2004 | Ogasawara et al. |
| 7,211,045 B2 | 5/2007 | Dala-Krishna et al. |
| 7,247,139 B2 | 7/2007 | Yudkovitch et al. |
| 7,300,406 B2 | 11/2007 | Carter |
| 7,303,530 B2 | 12/2007 | Barnes et al. |
| 7,393,326 B2 | 7/2008 | Bindefeld |
| 7,450,746 B2 | 11/2008 | Yang et al. |
| 7,539,532 B2 | 5/2009 | Tran |
| 7,686,766 B2 | 3/2010 | Quistgaard et al. |
| 7,697,982 B2 | 4/2010 | Brodnick |
| 7,713,208 B2 | 5/2010 | Kamiyama |
| 7,792,314 B2 | 9/2010 | Ramakrishnan et al. |
| 7,862,511 B2 | 1/2011 | Rafter |
| 7,981,038 B2 | 7/2011 | Kanade et al. |
| 7,987,303 B2 | 7/2011 | Bartlett |
| 8,057,390 B2 | 11/2011 | Witte et al. |
| 8,092,396 B2 | 1/2012 | Bagha et al. |
| 8,226,562 B2 | 7/2012 | Pelissier et al. |
| 8,241,217 B2 | 8/2012 | Chiang et al. |
| D675,738 S | 2/2013 | Baumer et al. |
| 8,388,538 B2 | 3/2013 | Younge et al. |
| 8,591,417 B2 | 11/2013 | Suzuki et al. |
| 8,622,910 B2 | 1/2014 | Kuban et al. |
| 8,680,991 B2 | 3/2014 | Tran |
| 8,764,660 B2 | 7/2014 | Frigstad et al. |
| 8,778,699 B2 | 7/2014 | Yerramilli et al. |
| 9,069,063 B2 | 6/2015 | Schreckenberg et al. |
| 9,078,571 B2 | 7/2015 | Bridger et al. |
| 9,089,278 B2 | 7/2015 | Salgo et al. |
| 9,161,721 B2 | 10/2015 | Yang |
| 9,192,352 B2 | 11/2015 | Yao et al. |
| 9,192,360 B2 | 11/2015 | Na et al. |
| 9,220,440 B2 | 12/2015 | Addison et al. |
| 9,237,881 B2 | 1/2016 | Chono et al. |
| 9,259,160 B2 | 2/2016 | Watson et al. |
| 9,301,032 B1 | 3/2016 | Bello et al. |
| 9,326,753 B2 | 5/2016 | Nishimura |
| 9,345,452 B2 | 5/2016 | Miyake |
| 9,349,098 B1 | 5/2016 | Ionson |
| 9,366,754 B2 | 6/2016 | Buckton et al. |
| 9,414,786 B1 | 8/2016 | Brockway et al. |
| 9,451,896 B2 | 9/2016 | Bauer |
| 9,545,228 B2 | 1/2017 | Bardy et al. |
| 9,561,015 B2 | 2/2017 | Halmann et al. |
| 9,662,504 B2 | 5/2017 | Dong et al. |
| 9,717,412 B2 | 8/2017 | Roham et al. |
| 9,746,448 B2 | 8/2017 | Gu |
| 9,901,252 B2 | 2/2018 | Tran |
| 9,907,535 B2 | 3/2018 | Barthe et al. |
| 10,507,009 B2 * | 12/2019 | Pagoulatos .......... A61B 8/0883 |
| 10,874,377 B2 * | 12/2020 | Pagoulatos ........ A61B 5/14551 |
| 2004/0225476 A1 | 11/2004 | Tien |
| 2004/0236223 A1 | 11/2004 | Barnes et al. |
| 2006/0004290 A1 | 1/2006 | Smith et al. |
| 2007/0186325 A1 | 8/2007 | Torrent Lopez et al. |
| 2008/0071184 A1 | 3/2008 | Carter |
| 2008/0281206 A1 | 11/2008 | Bartlett et al. |
| 2009/0312638 A1 | 12/2009 | Bartlett |
| 2010/0286527 A1 | 11/2010 | Cannon et al. |
| 2010/0331708 A1 | 12/2010 | Hatib |
| 2011/0213272 A1 | 9/2011 | Telfort et al. |
| 2011/0245651 A1 | 10/2011 | Nakamura |
| 2011/0275909 A1 * | 11/2011 | Kim ................... A61B 5/02007 600/301 |
| 2012/0065479 A1 | 3/2012 | Lahiji et al. |
| 2013/0053657 A1 | 2/2013 | Ziarno et al. |
| 2013/0123646 A1 | 5/2013 | Choi |
| 2013/0158363 A1 | 6/2013 | Zoghbi |
| 2013/0345563 A1 | 12/2013 | Stuebe et al. |
| 2014/0323865 A1 | 10/2014 | Hoppmann et al. |
| 2014/0336690 A1 | 11/2014 | Zhadkevich |
| 2014/0371574 A1 | 12/2014 | Shusterman et al. |
| 2015/0065814 A1 | 3/2015 | Kapoor |
| 2015/0065881 A1 | 3/2015 | Cho et al. |
| 2015/0086954 A1 | 3/2015 | Hoppmann et al. |
| 2015/0119758 A1 | 4/2015 | Rogers et al. |
| 2015/0223782 A1 | 8/2015 | Yamagata et al. |
| 2015/0293214 A1 | 10/2015 | Cannon et al. |
| 2015/0294085 A1 | 10/2015 | Kare et al. |
| 2015/0327775 A1 | 11/2015 | Carter |
| 2016/0045183 A1 | 2/2016 | Lee et al. |
| 2016/0066797 A1 | 3/2016 | Lee et al. |
| 2016/0100817 A1 | 4/2016 | Hussain |
| 2016/0143590 A1 | 5/2016 | Philipp et al. |
| 2016/0287207 A1 | 10/2016 | Xue |
| 2016/0296200 A1 | 10/2016 | Hinojosa |
| 2016/0338590 A1 | 11/2016 | Sagalovich et al. |
| 2016/0374571 A1 | 12/2016 | Narayan et al. |

(56) References Cited

U.S. PATENT DOCUMENTS

| | | |
|---|---|---|
| 2017/0014079 A1 | 1/2017 | Lee et al. |
| 2017/0086778 A1* | 3/2017 | Cahan ..................... A61B 7/02 |
| 2017/0112439 A1 | 4/2017 | Dubin et al. |
| 2017/0164930 A1 | 6/2017 | Oh et al. |
| 2017/0231508 A1 | 8/2017 | Edwards et al. |
| 2017/0252004 A1 | 9/2017 | Broad et al. |
| 2017/0262982 A1 | 9/2017 | Pagoulatos et al. |
| 2018/0000405 A1 | 1/2018 | Penders et al. |
| 2018/0049716 A1 | 2/2018 | Rajagopal et al. |
| 2018/0070913 A1 | 3/2018 | Sahin |

FOREIGN PATENT DOCUMENTS

| | | |
|---|---|---|
| RU | 2 539 990 C2 | 1/2015 |
| RU | 2015 152 075 A | 6/2017 |
| WO | 2005/013819 A1 | 2/2005 |
| WO | 2005/037096 A1 | 4/2005 |
| WO | 2006/082286 A1 | 8/2006 |
| WO | 2008/120154 A2 | 10/2008 |
| WO | 2012/158652 A2 | 11/2012 |
| WO | 2016/078992 A1 | 5/2016 |
| WO | 2016/207092 A1 | 12/2016 |

OTHER PUBLICATIONS

Russian Search Report for RU Application No. 2020114954/14(024839), dated Feb. 25, 2022, 2 pages.
Ramireddy et al., "Ultrasound Probe with Integrated ECG lead: Feasibility Study," Ultrasonic Imaging, 29, 195-198, 2007.
First Examination Report for Indian Application No. 202117020271, dated Dec. 14, 2022, 6 pages.

* cited by examiner

SYSTEM AND METHOD FOR FUSING ULTRASOUND WITH ADDITIONAL SIGNALS

BACKGROUND

Technical Field

The present application pertains to physiological sensing systems and methods, and more particularly to such systems and methods for acquiring and displaying ultrasound, electrocardiography, and auscultation data.

Description of the Related Art

Ultrasound imaging is typically performed in a clinical setting, by trained ultrasound experts, utilizing ultrasound systems that are specifically designed to acquire ultrasound data. Similarly, electrocardiography (EKG) is typically performed in a clinical setting by trained experts and utilizing equipment that is specifically designed for acquiring electrocardiography data. Auscultation data is typically acquired by a physician or other clinician utilizing a stethoscope.

Acquisition of these different types of clinical data, i.e., ultrasound data, EKG data, and auscultation data, is thus conventionally performed utilizing separate pieces of equipment, and often in separate patient visits or separate environments.

BRIEF SUMMARY

The present disclosure provides systems, methods and devices for acquiring or providing combined ultrasound, electrocardiography, and auscultation data. All three or any combination of two signals may be concurrently obtained by a single computing device connected to an ultrasound sensor, an electrocardiogram (EKG) sensor, and an auscultation sensor. The obtained signals may be synchronized with one another, such that the data obtained from the various sensors may be stored in a time-aligned manner. Alternatively or additionally, the obtained signals may be displayed in synchronization. Alternatively or additionally, the computing device may be configured such that each signal is obtained and displayed separately. Artificial intelligence techniques may be utilized to analyze the signals received from the ultrasound sensor, EKG sensor, and auscultation sensor to determine whether the signals, individually or in combination with one another, indicate one or more pathologies.

In at least one embodiment, a system is provided that includes an ultrasound sensor, an EKG sensor, an auscultation sensor, and a computing device. The computing device includes memory and a processor, and the processor is configured to receive and process signals from the ultrasound sensor, the EKG sensor, and the auscultation sensor.

In another embodiment, a handheld device is provided that includes a processor, a memory coupled to the processor, an ultrasound sensor, an EKG sensor, and an auscultation sensor. The ultrasound sensor, EKG sensor, and auscultation sensor are positioned on a sensing surface of the handheld device. Each of the ultrasound sensor, the EKG sensor, and the auscultation sensor are communicatively coupled to the processor.

In another embodiment, a method is provided that includes receiving by a computing device, ultrasound data, EKG data, and auscultation data; synchronizing at least two of the received ultrasound data, EKG data, and auscultation data; and storing the ultrasound data, EKG data, and auscultation data in memory.

In yet another embodiment, a system is provided that includes a computing device and an artificial intelligence (AI) data recognition module. The computing device is configured to acquire ultrasound data, EKG data, and auscultation data. The AI data recognition module is configured to receive the acquired ultrasound data, EKG data, and auscultation data and to automatically assess the data to produce a clinically-relevant determination based on a combined analysis of the data (e.g., automatically determine whether the received data indicates one or more pathologies).

In another embodiment, a handheld probe is provided that includes an ultrasound sensor positioned on a sensing surface of the probe, and an electrocardiogram (EKG) sensor positioned on the sensing surface of the probe.

DETAILED DESCRIPTION

Figure 1:
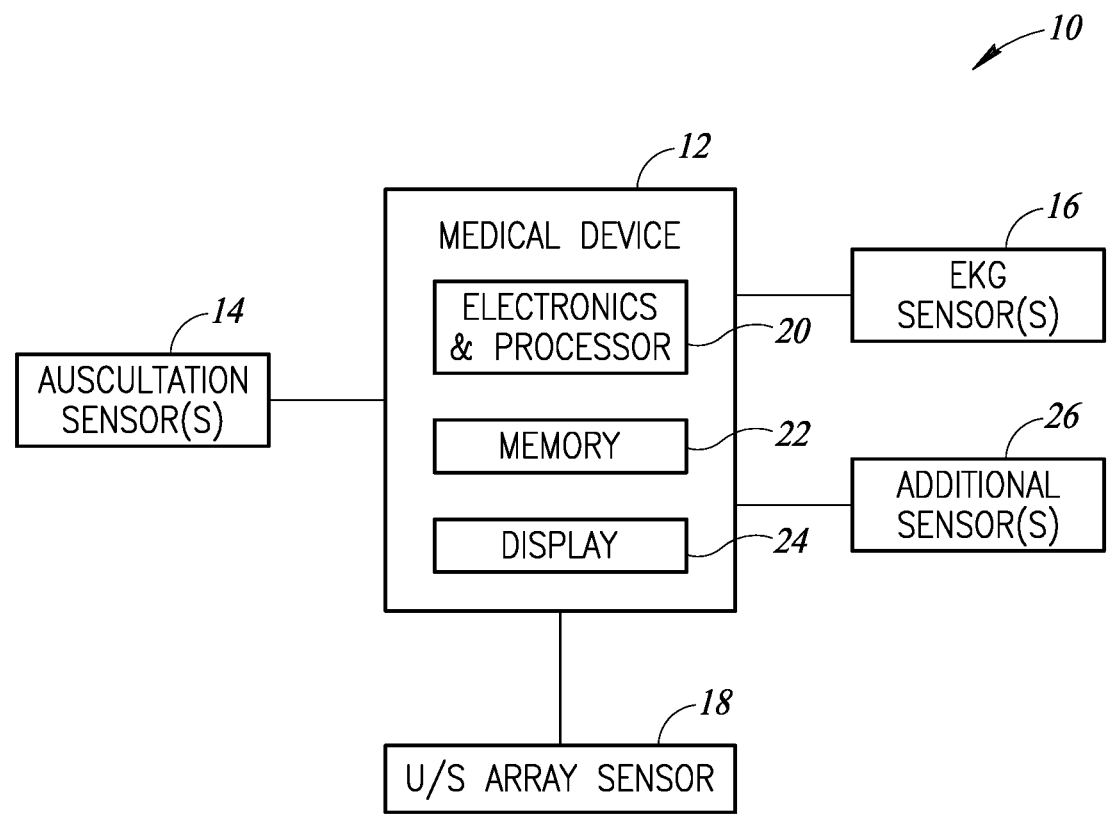
FIG. 1 is a block diagram illustrating a system for acquiring, synchronizing, and displaying a combination of ultrasound, electrocardiography, and auscultation signals, in accordance with one or more embodiments of the present disclosure.

Three primary techniques used extensively in medicine for physiological assessment, e.g., of the cardiothoracic cavity, include sonography, auscultation, and electrocardiography. Each technique provides different kinds of information usable to assess the anatomy and physiology of the organs present in a region of interest, e.g., the cardiothoracic cavity.

Medical ultrasound imaging (sonography) has been one of the most effective methods for examining both the heart and the lungs. Ultrasound imaging provides anatomical information of the heart as well as qualitative and quantitative information on blood flow through valves and main arteries such as the aorta and pulmonary artery. One significant advantage of ultrasound imaging is that, with its high frame rate, it can provide dynamic anatomical and blood flow information which is vital for assessing the condition of the heart which is always in motion. Combined with providing blood flow information, ultrasound imaging provides one of the best available tools for assessing the structure and function of heart chambers, valves, and arteries/veins. Similarly, ultrasound imaging can assess fluid status in the body and is the best tool in assessing pericardial effusion (fluid around the heart).

In the case of lungs, ultrasound imaging provides information on the anatomical structure of the lungs with the ability to show specific imaging patterns associated with various lung diseases and with an ability to assess fluid status around the lung and within individual compartments of the lung including the assessment of pericardial effusion.

Auscultation allows for assessing the physiological condition and function of organs such as the heart and lungs by capturing audible sounds that are produced by or otherwise associated with these organs. The condition and function of these organs, or other organs as the case may be, can be evaluated based on clinical information indicating how different sounds are associated with various physiological phenomena and how the sounds change for each pathological condition.

Electrocardiography (EKG or ECG) is focused on the heart by capturing the electrical activity of the heart as it is related to the various phases of the cardiac cycle. The condition and function of the heart may be evaluated based on clinical knowledge indicating how the electrical activity of the heart changes based on various pathological conditions.

The present disclosure provides systems, devices, and methods in which these three types of signals (i.e., auscultation, EKG, and ultrasound signals) are acquired and displayed (possibly in a synchronous manner) via one or more audiovisual outputs. Providing a combination of auscultation, EKG, and ultrasound data significantly enhances the ability of doctors and others to accurately and efficiently assess the physiological condition of a patient, especially of the patient's heart and lungs. Furthermore, by digitizing all three signals, analysis of such signals using digital signal processing is enabled, thereby allowing for implementation of various signal and image processing algorithms that can assess the signal data in combination. Such algorithms may include algorithms that are based on machine learning and pattern recognition to detect patterns in each of the three signals that are known to be associated with certain disease conditions.

When combined and jointly evaluated, the three signals may provide more insight into the physiological condition of a patient than would otherwise be provided by separate, individual assessment of each of the signals. That is, the combined acquisition and display of these signals provides additional information, particularly if the signals are synchronized, which ultimately results in significantly better sensitivity and specificity than would be obtained using any one signal alone. By combining these three signals in a synchronous manner, as described herein, analysis of the signals using machine learning is facilitated, including advanced methods such as deep learning, which provides a clear path for capturing expert physician knowledge associated with all three signals into the systems and devices.

This results in the ability of non-expert physicians and others to assess the physiological condition of a patient quickly with high sensitivity and specificity.

The systems and devices provided by the present disclosure allow for ultrasound, EKG, and auscultation sensors to be connected to a single computing device, digitized, stored in memory, and visualized through a user interface or display showing all three signals to the user, possibly in real-time as they are acquired. Furthermore, modules and methods are provided for synchronizing all three signals as they are acquired such that dynamic phenomena in the patient are properly captured and are time aligned for all three signals. The synchronization of the three signals has clinical importance in that, when physiological phenomena are properly represented by all three different signals and shown in a time-aligned manner, the information revealed in the ultrasound, audible sound, and electrical signals reflects conditions associated with the physiology at the same moment of time.

FIG. 1 is a block diagram illustrating a system 10 for acquiring ultrasound, electrocardiographic, and auscultation signals. The system 10 includes a computing device 12 (also referred to as a "medical device"), at least one auscultation sensor 14, at least one electrocardiogram (EKG) sensor 16, and at least one ultrasound sensor 18. One or more additional sensors 26 may further be included, for example a pulse oximeter sensor, although embodiments provided herein are not limited thereto. For example, the additional sensors 26 may include one or more of a gyroscope, a pressure sensor, a motion sensor, a temperature sensor, an EEG sensor, or any other type of sensor for sensing a physiological state, condition, or response of a patient, an environment around the patient, or a state or condition of the system 10.

The auscultation sensor 14, EKG sensor 16, and ultrasound sensor 18 are each communicatively coupled to the computing device 12 by a wired or wireless communication channel. The computing device 12 acquires, preferably digitizes, and processes the three types of signals, e.g., auscultation, EKG, and ultrasound signals.

The auscultation sensor 14 may be any sensor that detects internal body sounds of a patient, including, for example, body sounds associated with the circulatory, respiratory, and gastrointestinal systems. The auscultation sensor 14 has a sensor surface that may be placed in contact with a patient's skin in order to detect sound signals through the skin surface. The auscultation sensor 14 may be an electronic or digital stethoscope, and may include amplification and signal processing circuitry for amplifying and processing sensed signals, as may be known in the relevant field.

The EKG sensor 16 may be any sensor that detects electrical activity of a patient's heart, as may be known in the relevant field. For example, the EKG sensor 16 may include any number of electrodes, which in operation are placed on a patient's skin and used to detect electrical changes in the patient that are due to the heart muscle's pattern of depolarizing and repolarizing during each heartbeat.

The ultrasound sensor 18 includes a transducer configured to transmit an ultrasound signal toward a target structure in a region of interest in the patient. The transducer is further configured to receive echo signals returning from the target structure in response to transmission of the ultrasound signal. To that end, the transducer may include transducer elements that are capable of transmitting an ultrasound signal and receiving subsequent echo signals. In various embodiments, the transducer elements may be arranged as elements of a phased array. Suitable phased array transducers are known in the art.

The transducer array of the ultrasound sensor 18 may be a one-dimensional (1D) array or a two-dimensional (2D) array of transducer elements. The transducer array may include piezoelectric ceramics, such as lead zirconate titanate (PZT), or may be based on microelectromechanical systems (MEMS). For example, in various embodiments, the ultrasound sensor 18 may include piezoelectric micromachined ultrasonic transducers (PMUT), which are microelectromechanical systems (MEMS)-based piezoelectric ultrasonic transducers, or the ultrasound sensor 18 may include capacitive micromachined ultrasound transducers (CMUT) in which the energy transduction is provided due to a change in capacitance.

As shown in FIG. 1, the auscultation sensor 14, the EKG sensor 16, and the ultrasound sensor 18 may each be separately coupled to the computing device 12 via respective wired or wireless channels. For example, each of the auscultation sensor 14, the EKG sensor 16, and the ultrasound sensor 18 may be electrically and communicatively coupled to the computing device 12 by respective cables. In the case of the EKG sensor 16, which may include any number of electrodes, the electrodes may be coupled to the computing device 12 by leads. For example, the EKG sensor 16 may be a 10-electrode, 12-lead EKG sensor, although any EKG sensing configuration may be utilized as the EKG sensor 16 in accordance with the present disclosure. For example, the probe 140 shown in FIGS. 3A and 3B, described in greater detail below, includes an EKG sensor 116 with three electrodes.

In operation, a user of the system 10 may place each of the sensors 14, 16, 18 in a desired location in order to acquire signals, preferably simultaneously or during overlapping time intervals, from each of the sensors. For example, the EKG sensor 16 may include multiple electrodes, which may be placed in a suitable configuration on a patient's body, with the electrodes coupled to the computing device 12 by one or more leads. The user may place the auscultation sensor 14 at any desired location on the patient's skin, and similarly, may position the ultrasound sensor 18 as desired in order to obtain signals of interest. Accordingly, in operation, the computing device 12 may receive signals from each of the auscultation sensor 14, the EKG sensor 16, and the ultrasound sensor 18, preferably as the signals are each obtained.

The computing device 12 includes various electronics and a processor (referred to herein, collectively, as "electronics and processor 20" or in some cases simply "processor 20"). The electronics and processor 20 may include processing circuitry and driving circuitry. In part, the processing circuitry, or processor, controls the acquisition of signals from the auscultation sensor 14, the EKG sensor 16, and the ultrasound sensor 18.

For example, the electronics and processor 20 may include processing circuitry that controls the transmission of an ultrasound signal from the transducer elements of the ultrasound sensor 18, and driving circuitry that is operatively coupled to the transducer elements for driving the transmission of the ultrasound signal. The driving circuitry may drive the transmission of the ultrasound signal in response to a control signal received from the processing circuitry. The computing device 12 may further include a power supply that provides power to the electronics and processor 20, for example, to power the driving circuitry for transmission of the ultrasound signal. The electronics and processor 20 may similarly include processing circuitry that controls the acquisition of auscultation signals from the auscultation sensor 14, and controls the acquisition of EKG signals from the EKG sensor 16.

Additionally, the electronics and processor 20 may include signal processing circuitry, such as filters, amplifiers, preconditioning and digitization circuitry, and the like, which process the signals received from the auscultation sensor 14, the EKG sensor 16, and the ultrasound sensor 18. In particular, the electronics and processor 20 may include or otherwise implement a synchronization module for synchronizing the received signals, as will be discussed in further detail with respect to FIG. 4.

The electronics and processor 20 may include one or more application specific integrated circuits (ASICs) for providing or implementing the operations of the computing device 12 as described herein.

The computing device 12 shown in FIG. 1 further includes a memory 22 and a display 24. The memory 22 may be or include any computer-readable storage medium, including, for example, read-only memory (ROM), random access memory (RAM), flash memory, hard disk drive, optical storage device, magnetic storage device, electrically erasable programmable read-only memory (EEPROM), organic storage media, or the like. The memory 22 is coupled to the electronics and processor 20, which may execute programmed instructions that are stored in the memory 22 to perform the functions of the computing device 12 as described herein. Moreover, the memory 22 may store the signals acquired by the computing device 12. The signals may be stored in the memory 22 in a synchronized manner, or with associated information for synchronizing the signals, as will be discussed in further detail below with respect to FIG. 4.

The display 24 is an output interface that provides visual and/or audible information to a user of the computing device 12. The display 24 and/or the computing device 12 may include or be coupled to one or more speakers to provide audible information to the user. The display 24 may use, for example, any type of display technology including, but not limited to, an LED display technology. The display 24 may display signals acquired from the auscultation sensor 14, the EKG sensor 16, and the ultrasound sensor 18. More particularly, the display 24 may be used to display the signals and/or images acquired from the auscultation sensor 14, the EKG sensor 16, and the ultrasound sensor 18 in a synchronized manner, as will be discussed in further detail below with respect to FIGS. 4 and 5. In some embodiments, the display 24 may provide an input interface, such as a touch screen capable of receiving input from a user that touches the screen. In some embodiments, the computing device 12 may include one or more buttons, knobs, switches, and the like, capable of receiving input from a user of the computing device 12.

Figure 2:
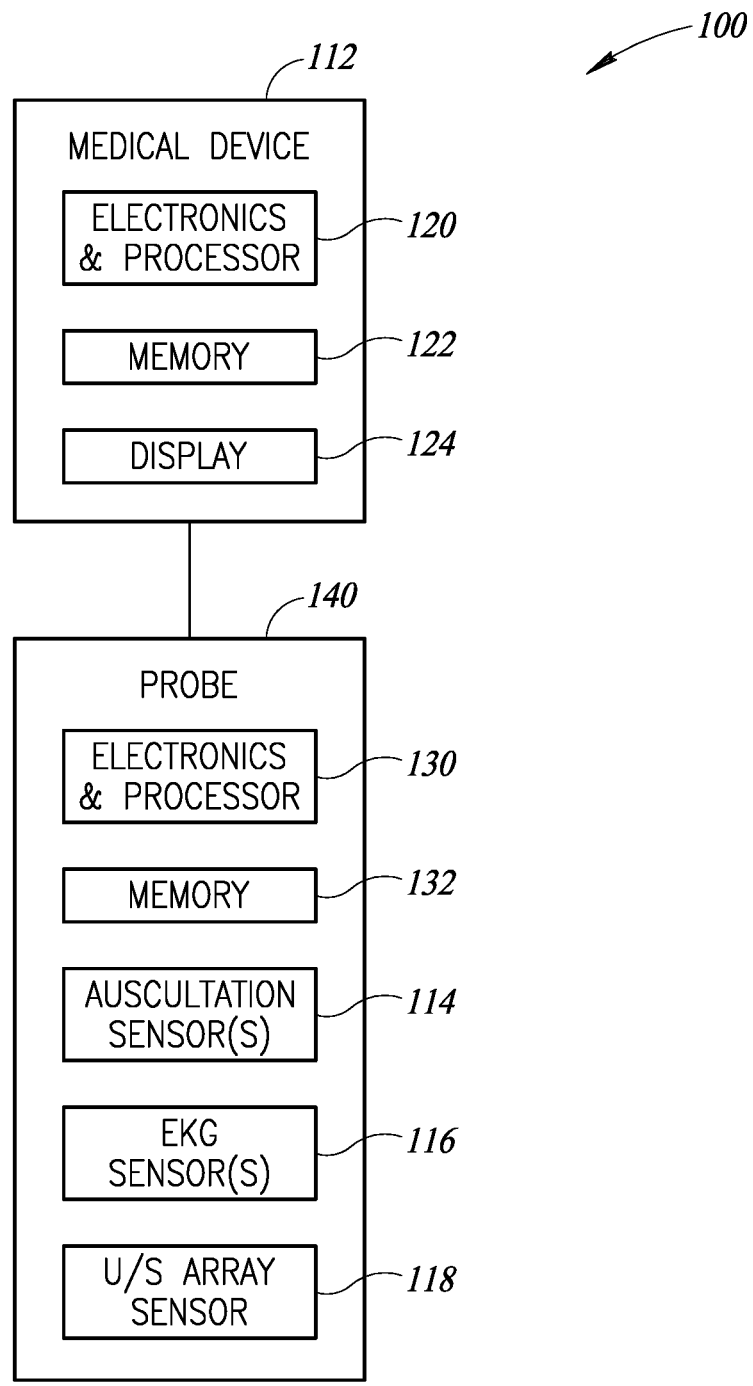
FIG. 2 is a block diagram illustrating a system for acquiring, synchronizing, and displaying a combination of ultrasound, electrocardiography, and auscultation signals, in accordance with one or more embodiments of the present disclosure.

FIG. 2 is a block diagram illustrating a system 100 for acquiring ultrasound, electrocardiographic, and auscultation signals. The system 100 is similar to the system 10 in many respects; however, a main difference between the system 100 of FIG. 2 and the system 10 of FIG. 1 is that, in the system 100, the auscultation sensor 114, the EKG sensor 116, and the ultrasound sensor 118 are all included in a probe 140, which is communicatively coupled to a computing device 112, e.g., by any wired or wireless communication channel. For example, the probe 140 may be coupled to the computing device 112 by one or more electrical cables.

Additionally, the probe 140 may itself include electronics and processor 130, which may be substantially the same as the electronics and processor 20 of the computing device 12 of FIG. 1. For example, the electronics and processor 130 in the probe 140 may include processing circuitry and driving circuitry that controls the acquisition of signals from the auscultation sensor 114, the EKG sensor 116, and the ultrasound sensor 118. In implementations where the probe 140 includes a power source, the probe may be operated separate from the computing device 112 to acquire ultrasound, electrocardiographic, and auscultation signal data from a patient, and later if desired, be communicatively coupled to the computing device 112 to upload the acquired signal data for further processing.

In some implementations, the probe 140 may be configured to use the electronics and processor 130 when the probe is operating separate from the computing device 112, but when the probe 140 is coupled (or "docked") to the computing device 112, the probe 140 may use some or all of the electronics and processor 120 in the computing device 112 in place of its own electronics and processor 130. This may be advantageous in cases where the electronics and processor 120 in the computing device 112 employs higher-quality components, such as a quieter power supply, more precise oscillator, and/or improved heat dissipation elements, or provides greater computational resources for generating, receiving, and/or processing the acquired signals or signal data.

For example, U.S. patent application Ser. No. 15/446,290, assigned to the assignee of the present disclosure and incorporated by reference herein, describes an ultrasound system that comprises an ultrasound probe and a docking station. The ultrasound probe is preferably a portable ultrasound probe, such as the handheld probe, that includes one or more first transducer elements that transmit an ultrasound signal toward a target structure in a region of interest. The ultrasound probe also includes processing circuitry that controls transmission of the ultrasound signal from the one or more first transducer elements and driving circuitry operatively coupled to the one or more first transducer elements and the processing circuitry. The driving circuitry drives the transmission of the ultrasound signal by the one or more first transducer elements in response to a control signal received from the processing circuitry. The ultrasound probe further includes one or more second transducer elements that receive echo signals returning from the target structure in response to transmission of the ultrasound signal, and a power supply that provides power to the driving circuitry for transmission of the ultrasound signal in at least a pulsed wave mode of operation.

The docking station includes an interface that allows coupling to the ultrasound probe. The docking station also includes circuitry that electrically couples to the ultrasound probe via the interface and enhances the ultrasound functionality of the ultrasound probe. In at least one embodiment, the docking station is provided separate from the ultrasound probe. In various embodiments, the circuitry in the docking station enhances the ultrasound functionality of the ultrasound probe by employing higher-quality components, such as a quieter power supply, oscillator, and/or heat dissipation elements or by providing greater computational resources for generating, receiving, and/or processing ultrasound signals or data.

The system described in U.S. patent application Ser. No. 15/446,290 may be adapted to further include auscultation and EKG signal acquisition as described herein, and provide a combined probe 140 according to the principles of the present disclosure. The auscultation and EKG signal acquisition of the combined probe 140 may similarly be enhanced when the combined probe 140 is electrically coupled or docked to the computing device 112.

Further, the probe 140 may include memory 132 that is coupled to the electronics and processor 130. The memory 132 may store the signals acquired by, and possibly digitized by, the electronics and processor 130. The auscultation, EKG, and ultrasound signal data may be stored in a synchronized manner, or with associated information for synchronizing the signals, as described herein.

The auscultation sensor 114, EKG sensor 116, and ultrasound sensor 118 may be similar to the auscultation sensor 14, EKG sensor 16, and ultrasound sensor 18 described above with respect to the system 10 of FIG. 1. However, some implementations may include certain differences as described herein with reference to FIG. 2 and FIGS. 3A and 3B.

Figure 3A:
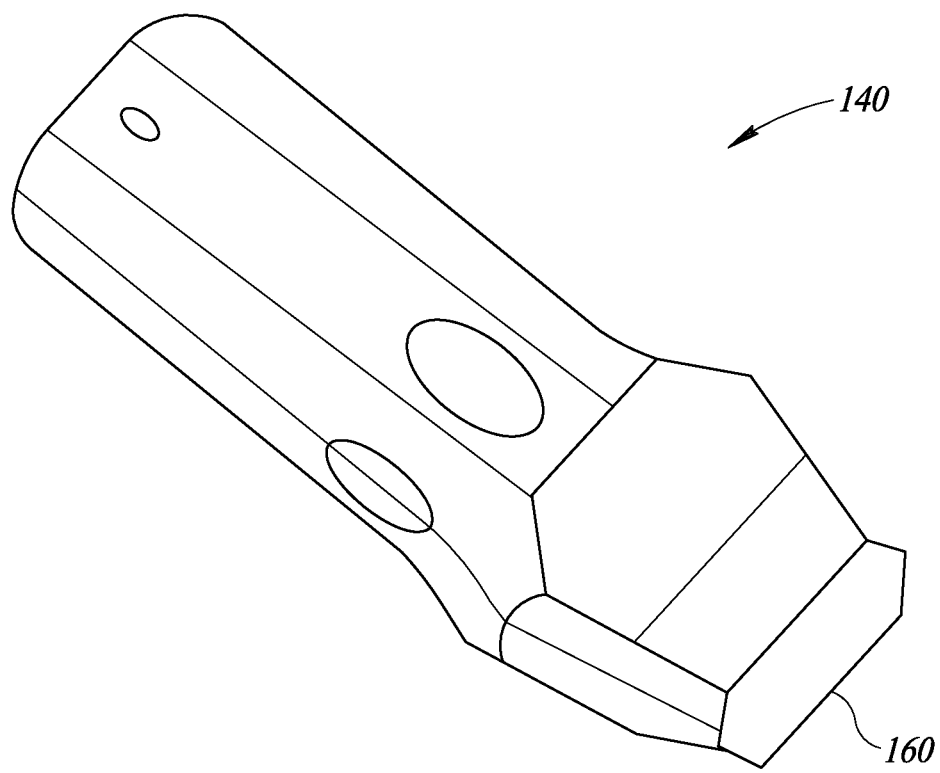
FIG. 3A is a perspective view of a probe that may be used in the system shown in FIG. 2, in accordance with one or more embodiments of the present disclosure.
Figure 3B:
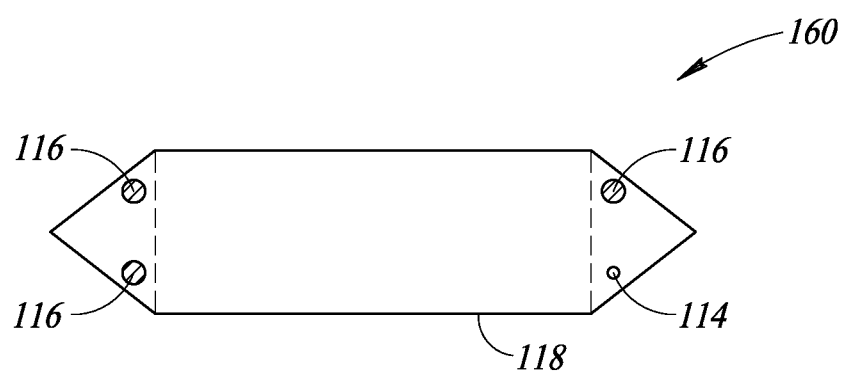
FIG. 3B is a front view of the probe shown in FIG. 3A, in accordance with one or more embodiments of the present disclosure.

FIG. 3A is a perspective view of at least one embodiment of the probe 140, and FIG. 3B is a front view of the embodiment shown in FIG. 3A, which illustrates a sensing surface 160 of the probe 140.

As shown in FIG. 3B, the auscultation sensor 114, EKG sensor 116, and ultrasound sensor 118 may be disposed on the sensing surface 160 of the probe. For example, the ultrasound sensor 118 (which may include an array of ultrasound transducers) may form a central portion of the sensing surface 160, while the EKG sensor 116 and the auscultation sensor 114 may be positioned on portions of the sensing surface 160 that extend outwardly from the central portion on which the ultrasound sensor 118 is positioned.

The auscultation sensor 114 may otherwise be substantially the same as the auscultation sensor 14 shown in FIG. 1, and may be any sensor for detecting internal body sounds of a patient, including, for example, body sounds associated with the circulatory, respiratory, and gastrointestinal systems. A plurality of auscultation sensors 114 may be provided on the sensing surface 160 of the probe 140. In such a case, one or more auscultation sensors 114 may be positioned on either or both sides of the ultrasound sensor 118. Any number of auscultation sensors 114 may be included in the probe 140 and positioned, for example, on the sensing surface 160.

The EKG sensor 116 may be any sensor for detecting the electrical activity of a patient's heart, as may be known in the relevant field. As shown in FIG. 3B, the EKG sensor 116 may include a plurality of electrodes arranged on the sensing surface 160 of the probe 140. In such a case, one or more EKG sensors 116 may be positioned on either or both sides of the ultrasound sensor 118. The EKG sensors 116 may preferably be positioned such that at least one EKG sensor 116 is positioned on each side of the ultrasound sensor 118, which provides a greater distance between the EKG electrodes.

The ultrasound sensor 118 includes a transducer, which may include transducer elements that are capable of transmitting an ultrasound signal and receiving subsequent echo signals as described above with respect to the ultrasound sensor 18 of FIG. 1.

In use, the sensing surface 160 of the probe 140 may be placed on a patient's skin, and auscultation, EKG, and ultrasound signals may be received, preferably simultaneously, by the probe 140. The acquisition of signals may be controlled by the electronics and processor 130 and stored in the memory 132 in the probe 140, in a manner that is the same or similar to that described above with respect to the electronics and processor 20 and memory 22 of FIG. 1.

In some embodiments, only the ultrasound sensor 118 and the EKG sensor 116 may be positioned on the sensing surface 160 of the probe 140, while in other embodiments, the auscultation sensor 114 may further be positioned on the sensing surface 160 of the probe 140.

Returning to FIG. 2, the computing device 112 shown in FIG. 2 includes electronics and processor 120 and memory 122. The electronics and processor 120 and memory 122 of the computing device 112 may control the acquisition of signals by the probe 140, in addition to or as an alternative to the acquisition of signals performed by the electronics and processor 130 and memory 132 of the probe. The electronics and processor 120 and memory 122 of the computing device 112 may also control operations of the computing device 112. For example, the electronics and processor 120 and memory 122 may receive signals from the probe 140, and cause the computing device 112 to display the signals and/or images associated with the signals on the display 124.

The computing device 112 may be, for example, a tablet computer, a PC or workstation computer, a mobile computing device such as a smartphone, or the like. The computing device 112 may communicate with the probe 140 over any wired or wireless communications channel, and may thus receive the signals acquired, processed and/or stored by the probe 140, and may display such signals or images associated with or derived from such signals.

In one or more embodiments, the probe 140 may include a display for displaying the acquired signals, images or clinical parameters associated with or derived from the acquired signals. In such a case, the computing device 112 may not be needed in order to acquire, process and display signals from the auscultation sensor 114, EKG sensor 116, and ultrasound sensor 118, as this may all be performed by the probe 140 itself.

Figure 4:
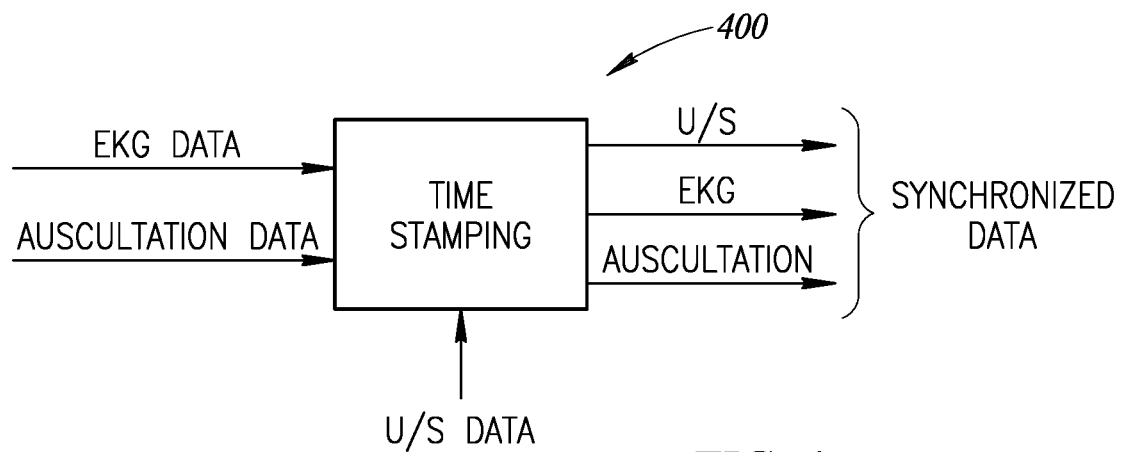
FIG. 4 is a block diagram illustrating a synchronization module that synchronizes data acquired from an auscultation sensor, an EKG sensor, and an ultrasound sensor, in accordance with one or more embodiments of the present disclosure.

FIG. 4 is a block diagram illustrating a synchronization module 400 that synchronizes signals or data that are simultaneously acquired from any two or more of an auscultation sensor, an EKG sensor, and an ultrasound sensor. In one or more embodiments, the synchronization module 400 may synchronize signals or data that is acquired from all three of the auscultation sensor, EKG sensor, and ultrasound sensor, as will be described herein. However, it will be readily appreciated that the embodiments provided herein are not limited to synchronization of signals from all three sensors, as the synchronization module may synchronize signals from any two or more of such sensors. With regard to the system 10 of FIG. 1, the synchronization module 400 may be included in or otherwise be accessible by the electronics and processor 20 and memory 22. In the system 100 of FIG. 2, the synchronization module 400 may be included in or otherwise accessible by the electronics and processor 130 and memory 132 in the probe 140 and/or may be included in or accessible by the electronics and processor 120 and memory 122 in the computing device 112.

As shown in FIG. 4, auscultation data, EKG data, and ultrasound data, which are derived from signals received by the auscultation sensor, EKG sensor, and ultrasound sensor, respectively, are provided to the synchronization module 400. In one embodiment, the synchronization module 400 synchronizes the auscultation data, EKG data, and ultrasound data by appending or associating time stamp information to each of these data. For example, the synchronization module 400 may include a clock (or otherwise have access to a clock) and may time stamp the data with time stamp information that indicates a time of receiving the data. The time stamp information may indicate a time with respect to a reference time, such as UTC time.

The synchronization module 400 may be coupled to memory (e.g., memory 22 of FIG. 1, or memory 122 or 132 of FIG. 2), such that the output data may be stored in the memory in a synchronized manner. For example, the data may be stored in the memory along with the associated time stamp information provided by the synchronization module 400. Alternatively or additionally, the synchronization module 400 may provide the auscultation data, EKG data, and ultrasound data to a remotely-located memory for storage in a synchronized manner.

In another embodiment, the synchronization module 400 does not append a time stamp to the received data, but instead associates the auscultation data, EKG data, and ultrasound data that are acquired at the same time and jointly stores the data in a combined manner in memory locations that are ordered or that may be retrieved based on the sequence in which the data is received. For example, auscultation data, EKG data, and ultrasound data that are acquired at a same point in time (e.g., time $t_1$) may be associated with one another by the synchronization module 400, and then stored in an ordered memory location. At a next point in time (e.g., at time $t_2$), the auscultation data, EKG data, and ultrasound data at that time may be associated with one another and stored in an ordered memory location that sequentially follows the memory location of the data acquired at time $t_1$. That is, the acquired data may be ordered based on a relative time that it was received by the synchronization module 400.

Figure 5:
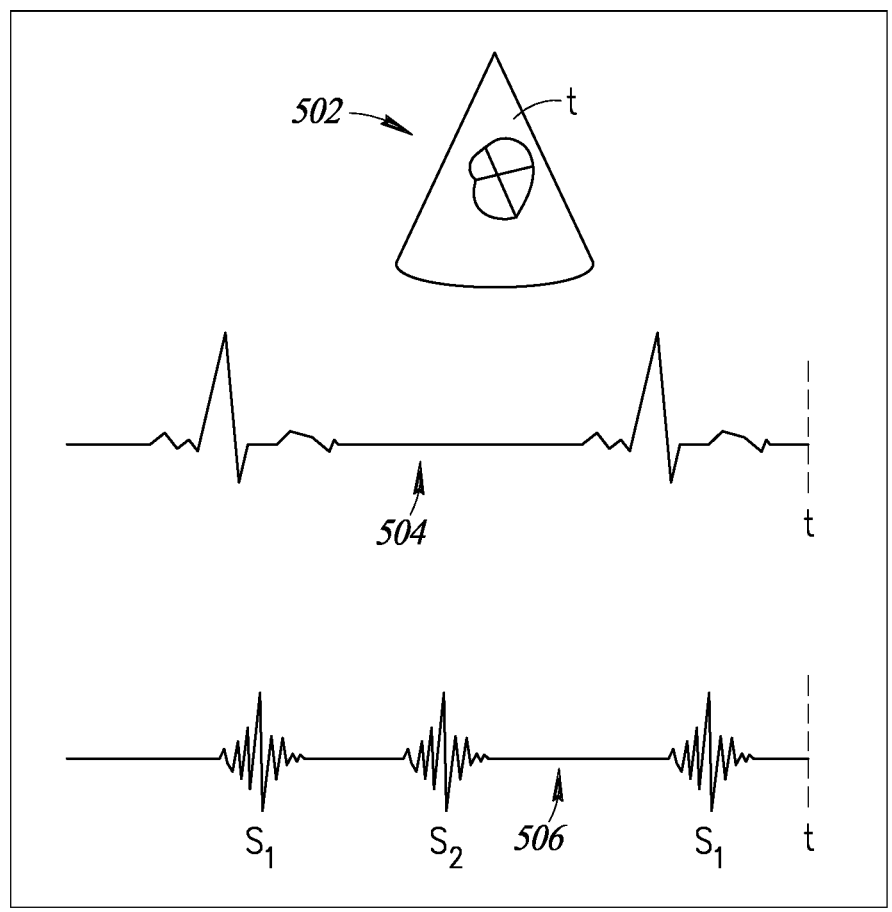
FIG. 5 is a pictorial diagram illustrating synchronous display of acquired ultrasound data, EKG data, and auscultation data, in accordance with one or more embodiments of the present disclosure.

FIG. 5 is a pictorial diagram illustrating synchronous display of the auscultation data, EKG data, and ultrasound data, which may be acquired by the separate auscultation sensor 14, EKG sensor 16, and ultrasound sensor 18 in the system 10, or which may be acquired by the combination auscultation sensor 114, EKG sensor 116, and ultrasound sensor 118 that are provided on a same sensing surface 160 of the probe 140 in the system 100. Synchronous display of the data may be provided on the display 24 of the computing device 12 of the system 10, on the display 124 of the computing device 112 of the system 100, or may be displayed on the probe 140 in embodiments where the probe includes a display.

As shown in FIG. 5, the ultrasound image 502 is shown for a particular point in time, t. The EKG waveform 504 at the time, t, is depicted by the dashed line. Similarly, the auscultation waveform 506 for the time, t, is depicted by the dashed line, which corresponds to the dashed line for the EKG waveform 504. As the signals in this embodiment are acquired in real-time, the ultrasound image 502 is sequentially updated (e.g., to reflect the current ultrasound image), and the EKG and auscultation waveforms 504, 506 grow from left to right with the dashed bar always indicating the time, t, that corresponds to the displayed ultrasound image 502.

The three auscultation, EKG, and ultrasound signals may be displayed in real-time, i.e., as they are acquired, or may be stored in memory in a synchronous manner, and later retrieved from memory and displayed in a synchronized display as shown in FIG. 5. Additionally, audio information may be provided in synchronization with the display of one or more of the auscultation data, EKG data, and ultrasound data. The audio information may be provided through one or more speakers. For example, the auscultation data may be output as audible information through one or more speakers in synchronization with the display of video information associated with the auscultation data.

The ultrasound data may be any ultrasound data associated with any ultrasound mode, including but not limited to, A-mode, B-mode, C-mode, M-mode, Doppler mode including continuous wave (CW) and pulsed wave (PW), and the like. The ultrasound data may be acquired in any ultrasound mode and may be displayed and/or provided as audible information in any ultrasound mode.

In one or more embodiments, artificial intelligence techniques may be employed in an artificial intelligence ("AI") data recognition module to analyze the auscultation, EKG, and ultrasound signals acquired by any of the devices or systems described herein. The analysis by the AI data recognition module may be based on any of the auscultation, EKG, and ultrasound signals individually, or may be based on any combination of these signals.

For example, U.S. patent application Ser. No. 15/454,678, assigned to the assignee of the present disclosure and incorporated by reference herein, describes various embodiments of artificial intelligence network systems and methods for ultrasound imaging, which utilize an ultrasound image recognition module to make determinations regarding acquired ultrasound images, such as determining whether (i) acquired ultrasound images accurately or substantially accurately depict or represent, or do not accurately or substantially accurately depict or represent, a desired view of a structure and/or anatomy including, for example, a patient's organ or other tissue, feature or region of interest in a patient, and (ii) whether acquired images representing clinically desired views of anatomy indicate normal function or a particular pathology.

The artificial intelligence techniques described in U.S. patent application Ser. No. 15/454,678 may be modified and implemented in embodiments of the present disclosure for similarly analyzing the acquired auscultation, EKG, and ultrasound signals and determining whether the signals indicate one or more pathologies. In at least one embodiment, AI parameters that are used to implement the artificial intelligence techniques are learned by processing training data obtained from auscultation, EKG, and ultrasound signals that are known to indicate one or more pathologies.

Figure 6:
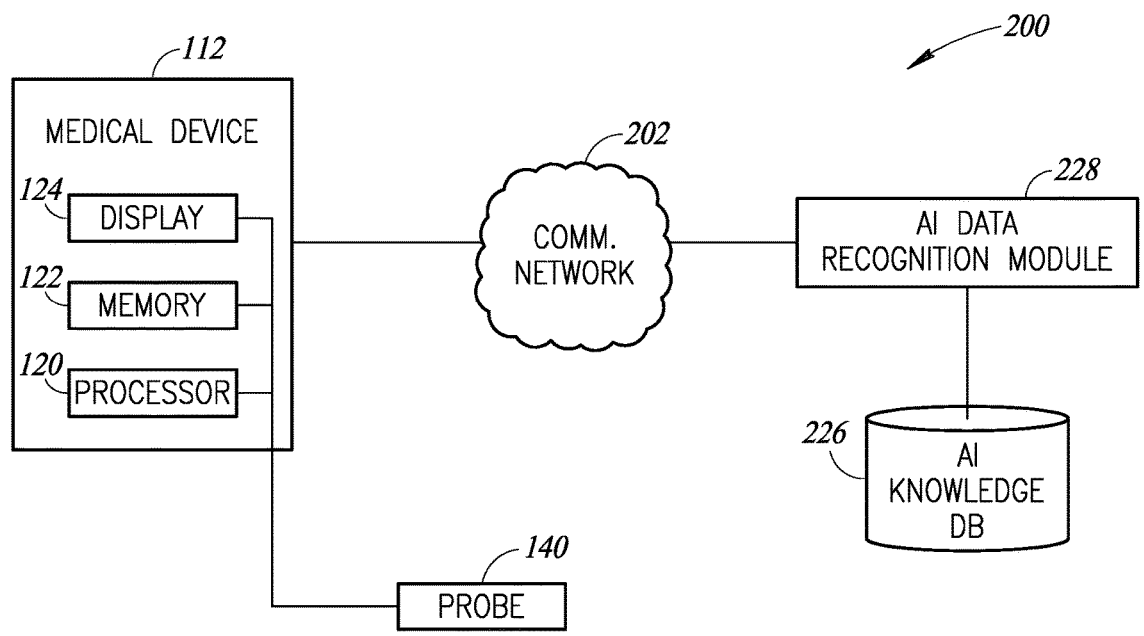
FIG. 6 is a block diagram illustrating a system for acquiring ultrasound, EKG, and auscultation signals that includes an artificial intelligence (AI) data recognition module, in accordance with one or more embodiments of the present disclosure.

FIG. 6 is a block diagram illustrating a system 200 for acquiring ultrasound, EKG, and auscultation signals, in accordance with embodiments of the present disclosure. The system 200 shown in FIG. 6 is similar to the system 100 shown in FIG. 2; however, one difference is that the system 200 further includes an AI data recognition module 228 for analyzing acquired auscultation, EKG, and ultrasound signals.

As shown in FIG. 6, the system 200 includes the computing device 112 and the probe 140, which may be the same as shown and described with respect to FIG. 2. In one or more embodiments, the system 200 may instead utilize the computing device 12 separately coupled to one or more of the auscultation sensor 14, the EKG sensor 16, the ultrasound sensor 18, and the additional sensors 26, as shown and described with respect to FIG. 1. In one or more embodiments, the system 200 may instead utilize probe 140 without the use of computing device 112.

The system 200 may further include a communications network 202, an AI data recognition module 228, and an AI knowledge database 226. One or both of the AI data recognition module 228 and AI knowledge database 226 may be incorporated into the computing device 112 or probe 140, or they may constitute multiple devices operatively and/or communicatively linked or linkable to one another.

As described with respect to FIG. 2, the probe 140 may be used to acquire auscultation data, EKG data, and ultrasound data. The acquired data may be provided to the AI data recognition module 228 via the communications network 202. Communications network 202 may utilize one or more protocols to communicate via one or more physical networks, including local area networks, wireless networks, dedicated lines, intranets, the Internet, and the like.

In one or more embodiments, the AI data recognition module 228 may be provided within the computing device 112, or a local implementation of the AI data recognition module 228 and/or knowledge stored in the AI knowledge database 226 may be contained within the computing device 112, with the computing device 112 having access to a remotely located (e.g., stored on one or more server computers, or in the "cloud") AI data recognition module 228, e.g., for receiving updated data recognition algorithms and/or knowledge.

The AI data recognition module 228 receives the auscultation, EKG, and ultrasound data acquired by the computing device 112, and makes determinations based on the acquired data. For example, the AI data recognition module 228 may determine whether the acquired data indicates normal function or a particular pathology. Such determinations may be made by the AI data recognition module 228 based on individual data signals (e.g., any one of the auscultation data, EKG data, or ultrasound data), or based on any combination of the acquired data signals.

The AI data recognition module 228 may be implemented by any computationally intelligent system that employs artificial intelligence, drawing from an AI knowledge database 226, to determine whether the acquired data indicates a particular pathology. Such determination may be performed automatically by the AI data recognition module 228, for example, in response to receiving the acquired auscultation, EKG, and ultrasound data.

"Artificial intelligence" is used herein to broadly describe any computationally intelligent systems and methods that can learn knowledge (e.g., based on training data), and use such learned knowledge to adapt its approaches for solving one or more problems. Artificially intelligent machines may employ, for example, neural network, deep learning, convolutional neural network, and Bayesian program learning techniques to solve problems such as image recognition. Further, artificial intelligence may include any one or combination of the following computational techniques: constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing one or more computationally intelligent techniques, the AI data recognition module 228 may learn to adapt to an unknown and/or changing environment for better assessment of the auscultation, EKG, and ultrasound signal data.

The AI knowledge database 226 may include a variety of information facilitating data analysis, with respect to received auscultation, EKG, and/or ultrasound data, by the AI data recognition module 228. In particular, the AI knowledge database 226 may contain information correlating particular auscultation, EKG, and/or ultrasound data to various pathologies. The AI knowledge database 226 may be stored in any computer-readable storage medium accessible by the AI data recognition module 228.

Figure 7:
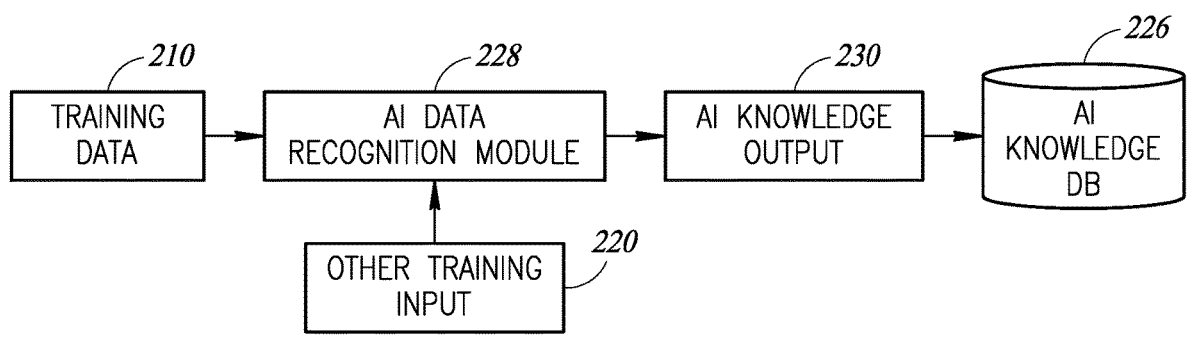
FIG. 7 is a block diagram illustrating training of the AI data recognition module shown in FIG. 6, in accordance with one or more embodiments.

FIG. 7 is a block diagram illustrating training of the AI data recognition module 228, in accordance with one or more embodiments. The AI data recognition module 228 may be trained based on training data 210. Training data 210 may include any auscultation, EKG, or ultrasound information. For example, the training data 210 may include a variety of auscultation data (e.g., audio waveforms) that are associated with particular pathologies, such as abnormal heart sounds that may be associated with heart murmurs or the like, abnormal lung sounds such as wheezes, crepitations or the like, or any other body sounds that may be associated with one or more pathologies. Similarly, the training data 210 may include a variety of EKG data (e.g., electrical waveforms) that are associated with particular pathologies, such as arrhythmia, myocardial infarction, pulmonary embolism or the like. The training data 210 may further include a variety of ultrasound data (e.g., ultrasound image data) associated with known views of an organ, such as the heart, as well as ultrasound data associated with particular pathologies.

Other training input 220 may further be provided to the AI data recognition module 228 for training. The other training input 220 may include, for example, manually-entered input to adjust or otherwise manage the data recognition model developed in the AI data recognition module 228 through the training process.

Using training data 210, the AI data recognition module 228 may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, and/or recording learning.

As a result of the training, the AI data recognition module 228 may learn to modify its behavior in response to the training data 210, and obtain or generate AI knowledge 230. The AI knowledge 230 may represent any information upon which the AI data recognition module 228 may determine an appropriate response to new data or situations. In particular, the AI knowledge 230 represents relationships between auscultation, EKG, and ultrasound data and one or more pathologies. The AI knowledge 230 may be stored in the AI knowledge database 226.

Based on the training data 210, the AI recognition module 228 may learn to modify its behavior, and may apply knowledge contained in the AI knowledge database 226 to alter the manner in which it makes determinations with respect to new input, such as, for example, auscultation, EKG, and ultrasound data received by the computing device 112. The AI data recognition module 228 may apply the acquired knowledge to incoming auscultation, EKG, and ultrasound data, and automatically assess the data to produce one or more clinically-relevant determinations based on a combined analysis of the data. For example, the AI recognition module 228 may automatically determine whether the received data indicates one or more specific pathologies.

In one or more embodiments, the present disclosure provides a system that includes: a computing device configured to acquire ultrasound data, electrocardiogram (EKG) data, and auscultation data; and an artificial intelligence (AI) data recognition module configured to receive the acquired ultrasound data, EKG data, and auscultation data and to automatically determine whether the received data, in any combination, indicates one or more pathologies.

The system may further include a synchronization module communicatively coupled to the computing device, and the synchronization module may be configured to synchronize two or more of the acquired ultrasound data, EKG data, and auscultation data.

The AI data recognition module may be configured to determine whether the synchronized two or more of the acquired ultrasound data, EKG data, and auscultation data indicates one or more pathologies.

In one or more embodiments, the present disclosure provides a handheld probe that includes: an ultrasound sensor positioned on a sensing surface of the probe; and an electrocardiogram (EKG) sensor positioned on the sensing surface of the probe.

The handheld probe may further include: a processor; and a memory coupled to the processor, wherein the ultrasound sensor and the EKG sensor are communicatively coupled to the processor. The EKG sensor may include a plurality of electrodes positioned on the sensing surface of the probe.

The various embodiments described above can be combined to provide further embodiments. All of the U.S. patent applications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A handheld device, comprising:
processing circuitry;
an ultrasound sensor; and
at least one of an electrocardiogram (EKG) sensor or an auscultation sensor,
wherein the ultrasound sensor and the at least one of the EKG sensor or the auscultation sensor are configured to acquire respective signals of a patient, and the processing circuitry is configured to digitize and synchronize the acquired signals, and
wherein the processing circuitry is configured to implement an artificial intelligence (AI) data recognition module, the AI data recognition module configured to automatically determine whether the synchronized signals, in any combination, indicate one or more pathologies.

2. The handheld device of claim 1, further comprising a display communicatively coupled to the processing circuitry, the display configured to display the synchronized signals in a time-aligned manner.

3. The handheld device of claim 1, wherein the handheld device includes both of the EKG sensor and the auscultation sensor, wherein the ultrasound sensor, the EKG sensor, and the auscultation sensor are configured to acquire respective signals of the patient, and the processing circuitry is configured to digitize and synchronize the acquired signals from each of the ultrasound sensor, the EKG sensor, and the auscultation sensor.

4. The handheld device of claim 3, wherein at least two of the ultrasound sensor, the EKG sensor, and the auscultation sensor are configured to simultaneously acquire respective signals of the patient.

5. The handheld device of claim 1, wherein the processing circuitry includes a clock, and the processing circuitry is configured to digitize and synchronize the acquired signals based on the clock.

6. The handheld device of claim 1, wherein the ultrasound sensor includes piezoelectric micromachined ultrasonic transducers or capacitive micromachined ultrasound transducers.

7. The handheld device of claim 1, wherein the ultrasound sensor and the at least one of the EKG sensor or the auscultation sensor are configured to acquire the respective signals of the patient during overlapping time intervals, and the processor is configured to synchronize the acquired signals in a time-aligned manner.

8. A computing device, comprising:
processing circuitry configured to:
receive ultrasound signals from an ultrasound sensor of a handheld probe;
receive electrocardiogram (EKG) signals from an EKG sensor of the handheld probe;
receive auscultation signals from an auscultation sensor of the handheld probe; and
synchronize the received signals,
wherein the processing circuitry is configured to implement an artificial intelligence (AI) data recognition module, the AI data recognition module configured to automatically determine whether the synchronized signals, in any combination, indicate one or more pathologies.

9. The computing device of claim 8, further comprising a display configured to synchronously display an ultrasound image, an EKG waveform, and an auscultation waveform, based on the synchronized signals.

10. The computing device of claim 8, wherein the processing circuitry includes a clock, and the processor is configured to synchronize the received signals based on the clock.

11. The computing device of claim 10, wherein the processing circuitry is configured to time stamp the received signals.

12. The computing device of claim 8, further comprising a memory communicatively coupled to the processing circuitry, the memory configured to store the synchronized signals.

13. A system, comprising:
a computing device configured to:
receive ultrasound signals from an ultrasound sensor;
receive at least one of electrocardiogram (EKG) signals from an EKG sensor or auscultation signals from an auscultation sensor; and
synchronize the received signals; and
processing circuitry configured to implement an artificial intelligence (AI) data recognition module, the AI data recognition module configured to receive the synchronized signals and to automatically determine whether the synchronized signals, in any combination, indicate one or more pathologies.

14. The system of claim 13, further comprising a handheld probe, the handheld probe including the ultrasound sensor and at least one of the EKG sensor or the auscultation sensor.

15. The system of claim 14, wherein the handheld probe includes the ultrasound sensor, the EKG sensor, and the auscultation sensor, wherein the handheld probe is configured to simultaneously acquire the ultrasound signals, the EKG signals, and the auscultation signals.

16. The system of claim 13, wherein the computing device includes a display configured to display the synchronized signals.

17. The system of claim 13, further comprising:
a database storing information correlating a plurality of pathologies with ultrasound data, EKG data, and auscultation data, wherein the AI data recognition module is configured to determine whether the synchronized signals indicate one or more pathologies based on the information stored in the database.

18. The system of claim 13, wherein the AI data recognition module is trained based on training data, the training data including ultrasound data associated with one or more pathologies, EKG data associated with one or more pathologies, and auscultation data associated with one or more pathologies.

19. The system of claim 13, wherein the training data includes data associated with at least one of: abnormal heart sounds, heart murmurs, abnormal lung sounds, lung wheezing, crepitation, abnormal heart waveforms, arrhythmia, myocardial infarction, pulmonary embolism, or known views of an organ.

* * * * *